United States Patent [19]  [11] 4,333,478
Krieg  [45] Jun. 8, 1982

[54] BLOOD EXTRACTION INSTRUMENT

[75] Inventor: Karl Krieg, Nuertingen, Fed. Rep. of Germany

[73] Assignee: C.A. Greiner & Sohne GmbH & Co. KG, Nuertigen, Fed. Rep. of Germany

[21] Appl. No.: 196,721

[22] Filed: Oct. 14, 1980

[30] Foreign Application Priority Data

Nov. 20, 1979 [DE] Fed. Rep. of Germany ....... 2946680

[51] Int. Cl.$^3$ .............................................. A61B 5/14
[52] U.S. Cl. ................................................... 128/764
[58] Field of Search ............... 128/763, 764, 765, 766, 128/218 N, 216, 221

[56] References Cited

U.S. PATENT DOCUMENTS

| 3,433,216 | 3/1969 | Mattson | 128/764 |
| 3,877,465 | 4/1975 | Miyake | 128/764 |
| 4,154,229 | 5/1979 | Nugent | 128/764 |
| 4,166,450 | 9/1979 | Abramson | 128/764 |

FOREIGN PATENT DOCUMENTS 1278387 12/1961 France .............................. 128/764

Primary Examiner—John D. Yasko
Attorney, Agent, or Firm—Michael F. Petock

[57] ABSTRACT

A blood extraction instrument is provided with an adjustably rotatable connector for a double-ended hollow needle which is offset mounted through the closed end of the cylindrical body of the instrument. The end of the double-ended hollow needle which extends into the instrument pierces a membrane on the end of a blood sample tube which is retained thereon by means of a screw-on cap. The other end of the double-ended hollow needle, which is on the exterior of the instrument, is for insertion into a blood vessel, that is a vein, of a patient. This end is provided with an obliquely cut point. In accordance with the adjustably rotatable connector, the orientation of the flat surface of the needle point which penetrates the patient may be readily adjusted. The instrument is also provided with a retaining tongue formed by a slot in the cylindrical wall of the instrument for providing a retaining means against the back side of the screw-on cap to retain the blood sample tube in the instrument.

10 Claims, 6 Drawing Figures

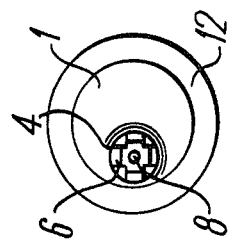
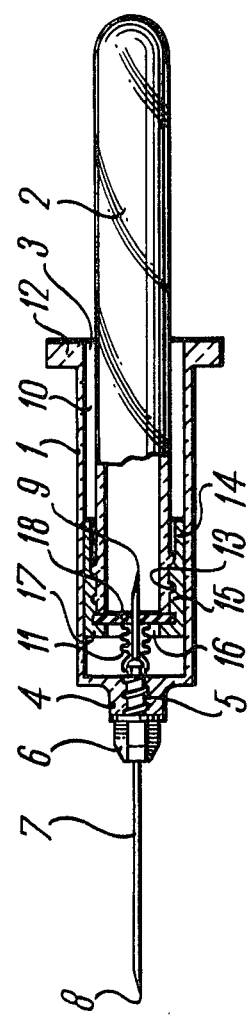

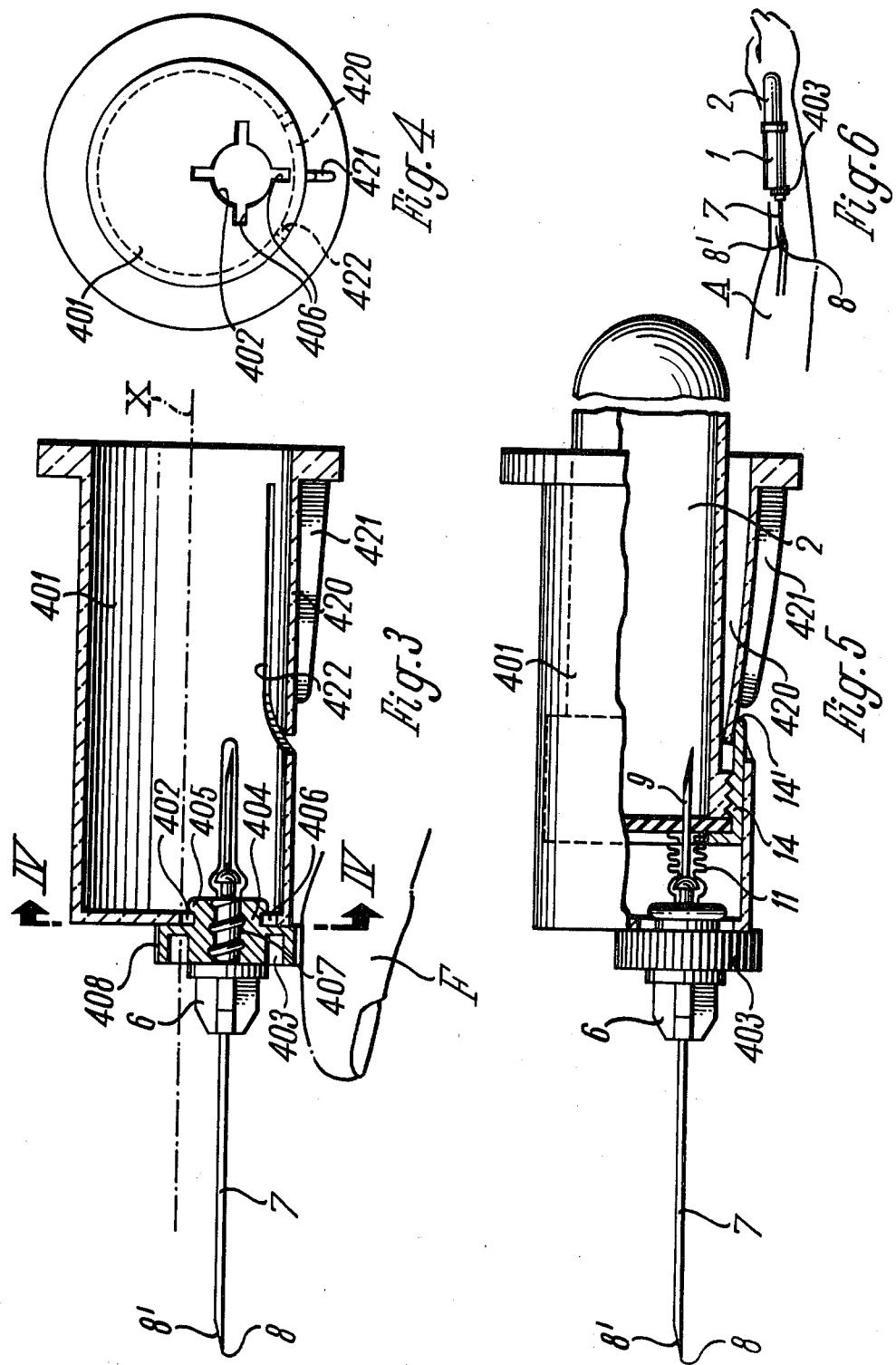

BLOOD EXTRACTION INSTRUMENT

BACKGROUND OF THE INVENTION

The present invention is directed to a blood extraction instrument. More particularly, the present invention is directed to an improvement in the blood extraction instrument described in U.S. patent application Ser. No. 127,709, filed on Mar. 6, 1980. More particularly, the present invention is directed to an improvement wherein the obliquely cut point of the hollow needle which is inserted into the patient's blood vessel may be readily adjusted to provide optimum insertion into the patient, and further to provide a means of insuring that the blood sample tube is retained in the instrument as desired during the procedure.

In accordance with the aforesaid U.S. patent application Ser. No. 127,709, a blood extraction instrument is provided with a hollow, cylindrical body having a closed and an open end. The open end of the cylindrical body is adapted to receive a blood sample tube. The blood sample tube is closed at the insertion end by a membrane which is retained thereon by a screw-on cap. At the closed end of the instrument, a double-ended hollow needle is mounted therein. One end, the end inside of the instrument, pierces the membrane of the blood sample tube when the blood sample tube is inserted into the hollow, cylindrical body. The other end of the double-ended hollow needle is located outside of the hollow, cylindrical body of the instrument, and is obliquely cut to provide a point which is inserted into the patient's blood vessel.

The double-ended hollow needle is eccentrically mounted on the closed end of the body of the instrument. This has been made possible by the closing of the blood sample tube by means of a screw-on cap and membrane. The eccentric location of the needle has a significant advantage in that it is possible to insert the needle into the blood vessel of the patient at a very small acute angle. In other words, it is advantageously provided that the angle that the needle makes with the blood vessel into which it is to be inserted is an acute angle, or in other words, that it is more nearly parallel to the blood vessel than perpendicular.

However, a difficulty is encountered in this technological development in that care must always be exercised to insure that outer needle point, having the obliquely cut face, be positioned with a specific orientation. The obliquely cut surface of the needle point should be turned towards the axis of the cylindrical body of the instrument, or in other words, turned away from the patient's surface of insertion. In order to insure the advantage of the eccentric location of the needle, it is necessary that the proper positioning be provided. However, from the manufacturing point of view, it is extremely difficult to insure that the thread of the portion of the needle which is screwed into the body, as well as the thread provided in the cylindrical body of the instrument are always so arranged that this particular orientation is achieved when the needle is held firmly in place. This is particularly a problem as the cylindrical body of the blood extraction instrument is used repeatedly by health care professionals, and therefore, there can be no guarantee, even if it is properly positioned when it leaves the factory, that it will continue to be properly positioned in future use.

SUMMARY OF THE INVENTION

It is an intended advantage of the present invention to provide a blood extraction instrument of the type initially mentioned, where the desired orientation of the needle point is always readily obtainable.

In accordance with the present invention, the double-ended hollow needle is mounted in an adjustable connector, which may be rotated inside of the opening or aperture in the closed end of the cylindrical body.

The connector may be readily mounted in the aperture in the closed end of the cylindrical body of the instrument by means of a hub on the connector having a retaining bead, with slots provided either in the closed end about the aperture or radially extending through the hub and retaining bead.

In accordance with the present invention, the needle is no longer screwed directly into the cylindrical body of the instrument, but rather into a connector which mounts into the body of the instrument and is rotatably adjustable. It is therefore extremely easy for the health care professional to obtain the desired orientation of the needle point by means of a simple maneuver.

In accordance with the present invention, means is also provided to ensure that the blood sample tube is retained in the blood extraction instrument during the desired blood extraction.

BRIEF DESCRIPTION OF THE DRAWINGS

For the purpose of illustrating the invention, there are shown in the drawings forms which are presently preferred; it being understood, however, that this invention is not limited to the precise arrangements and instrumentalities shown.

FIG. 1 is a cross-sectional view of the blood extraction instrument utilizing a hollow double-ended needle and a blood sample tube.

FIG. 2 is an elevation view of the closed end of the blood extraction instrument in accordance with FIG. 1.

FIG. 3 is a cross-sectional view of a blood extraction instrument in accordance with the present invention.

FIG. 4 is an elevation view taken along line IV—IV of FIG. 3 showing the closed end of the blood extraction instrument with the aperture therein for receiving the connector.

FIG. 5 is an elevation view, partially in cross-section, of a blood extraction instrument in accordance with the present invention having a blood sample tube inserted therein and retained therein by a retaining tongue.

FIG. 6 is a schematic of a blood extraction instrument in accordance with the present invention in use in a blood extraction procedure.

DETAILED DESCRIPTION OF THE PREFERRED EMBODIMENT

The blood extraction instrument illustrated in FIGS. 1 and 2 is in accordance with U.S. patent application Ser. No. 127,709, assigned to the assignee of the invention of this application. As illustrated in FIGS. 1 and 2, the blood extraction instrument is comprised of a body 1 and a blood sample tube 2. The body 1 has a hollow, cylindrical shape and is open at one end 3. At the other end 4, the body 1 is provided with a threaded bore 5 eccentrically mounted on end 4. Needle holder 6 is threadably mounted into threaded bore 5. Needle holder 6 serves to firmly mount double-ended needle 7, of which one end 8 is located outside body 1 in the manner as shown in FIG. 1. The end 3 outside body 1 is adapted to be inserted into a blood vessel, particularly a vein, of a person for the purposes of extraction of blood, see FIG. 5. The other end 9 of double-ended needle 7 extends into the cylindrical, hollow interior of body 1. The portion of needle 7 which extends into the interior 10 of body 1 is covered by a protective covering 11 comprised of a light and soft material which may be easily penetrated. At the open end 3, body 1 is provided with a flange 12 which facilitates handling during blood extraction.

Blood sample tube 2, which is preferably manufactured from a transparent synthetic material, is provided with a screw closure. The screw closure in the embodiment as described is provided by a screw-on cap 14 which is provided with internal threads 15 for mounting on the left end or open end 3 of blood sample tube 2 which is provided with external threads 13. Screw-on cap 14 has an opening 16. The diameter of opening 16 is selected to provide a sufficient edge 17 extending inwardly towards the longitudinal axis of blood sample tube 2 to provide sufficient pressure on membrane 18 to maintain membrane 18 tightly against the open or front rim of blood sample tube 2. In this manner, the interior of blood sample tube 2 is closed so that a vacuum may be maintained in blood sample tube 2.

For use in blood extraction from a patient, the blood extraction instrument is taken in the hand of the health care professional with the end 8 of needle 7 being inserted into the vein or other appropriate blood vessel of the patient, which may be in a manner substantially as shown in FIG. 6. Thereafter, blood sample tube 2 is inserted into the body 1 of the blood extraction instrument. The blood sample tube 2 is evacuated shortly before being inserted. It is inserted sufficiently far into hollow, cylindrical body 1 so that the inner end 9 of needle 7 penetrates membrane 18. This position of blood sample tube 2 is shown in FIG. 1. In this position, the vacuum in the blood sample tube extracts blood from the vein. FIG. 2 illustrates that the needle 7 is eccentrically positioned on the closed end of body 1.

FIGS. 3 through 5 illustrate embodiments of the present invention. In accordance with the present invention, the needle 7 or needle holder 6 can be rotated so that point 8 of needle 7 may always have optimal orientation for insertion into the patient's blood vessel. As shown in FIG. 5, optimal orientation is achieved when the eccentric positioning of the needle in the holder may be utilized for inserting the needle into the patient's vein or other appropriate blood vessel at as an acute an angle as possible. In other words, the angle between the surface of insertion or the blood vessel into which it is being inserted and the needle should be as small as possible. In other words, the line of the needle and the surface of the patient should be as close as possible to parallel, as contrasted to being perpendicular. This method of insertion is illustrated in FIG. 6 with the example of the arm A of a patient. It is necessary to turn the holder so that the needle lies as closely as possible to the surface of this part of the patient's body. Then, however, the orientation of the needle must be such at point 8, which is obliquely cut at an acute angle, so that cut surface 8' is oriented towards the longitudinal axis X of body 1 of the instrument (see FIG. 3). In other words, the flat surface 8' of the point 8 of needle 7 should preferably point away from the body of the patient at the time of insertion. In the past, it was required, with some difficulty, to determine the threading of the bore 5 and the outside threading of the needle holder in such a manner that such orientation of cut surface 8' of the point 8 of needle 7 was always obtained. This was particularly a problem as the blood extraction instrument was intended to be used repeatedly by health professionals.

In accordance with the present invention, FIGS. 3 and 4 illustrate an adjustably rotatable connector 403, in the form of a ring, which is inserted into opening 402 in body 401. The adjustable connector 403 has a hub 404, the end of which is provided with a clamp or retaining bead 405. Opening 402 is provided with slots 406 enabling a slightly larger item to be forced therethrough. Because of slots 406, the retaining bead 405 on hub 404 of connector 403 may be pushed into opening 402. Alternatively, instead of slots 406 being formed radially extending outward from aperture 402, radial slots may be provided in hub 404 and retaining bead 405 to enable compression of the retaining bead to be forced through an unslotted aperture in body 401. In other words, the slots in hub 404 would make it possible to deform the hub 404 with retaining bead 405 by compression when it is pushed into an unslotted opening 402, or even a slotted opening 402. Threaded bore 407 is provided in adjustable connector 403, and needle holder 6 is screwed into this.

About the exterior circumference of adjustable connector 403, knurling 408 is provided. In order to enhance the ease with which connector 403 is rotated to adjust the orientation of point 8, the outer circumference or edge of adjustable connector 403 extends at least to the edge of body 401 and preferably extends at least slightly beyond the circumference of body 401 at at least one point. As may be seen in FIG. 3, projection of the knurled edge 408 beyond the circumference of body 401 enables connector 403 to be readily rotated to properly adjust the orientation of point 8 by means of a finger F as shown in FIG. 3.

Even though needle holder 6 is screwed into adjustable connector 403, the desired orientation of the obliquely cut surface 8' of needle point 8 may be obtained by mere rotation of connector 403. Opening 402 is dimensioned to provide a light clamping effect by the circumferential edge of aperture 402 on the adjustably rotatable connector 403 when it is inserted. In other words, rotation is readily possible, but on the other hand, the clamping effect is sufficient to hold the connector 403 securely at the adjusted position.

As may be seen in FIG. 3, a slot 422 is cut into body 401. This results in a retaining tongue 420 in body 401. When blood sample tube 2 is inserted into body 401, retaining tongue 420 is pushed somewhat inwardly by hand. This will grip behind the edge of screw-on cap 14 and prevent the possibility of blood sample 2 being pushed out of body 401 by the elastic counter-pressure force of protective covering 11. It is therefore possible to lock blood sample tube 2 in body 401 by means of a retaining tongue 420. In order to unlock it, blood sample tube 2 is pushed somewhat further into body 401. This causes retaining tongue 420 to spring back to its initial position (see FIG. 3). Blood sample tube 2 may then be taken out of body 401 without obstruction. In order to increase the spring back force of retaining tongue 420, it is provided with a reinforcement rib 421. In order to facilitate the ripping of the front side of tongue 420 at the left in FIG. 5, behind the edge of the screw-on cap 14, the latter is rounded, as may be seen at 14'.

The present invention may be embodied in other specific forms without departing from the spirit or essential attributes thereof and, accordingly, reference should be made to the appended claims, rather than to the foregoing specification as indicating the scope of the invention.

I claim:

1. A blood extraction instrument, comprising:
a hollow, cylindrical body having an open end and a closed end, the open end being adapted to receive a blood sample tube, said blood sample tube being closed with a membrane by means of a screw-on cap, said screw-on cap being provided with an opening for exposure of said membrane, means for mounting a double-ended hollow needle in said closed end of said cylindrical body, one end of said double-ended hollow needle being positioned to penetrate said membrane of said blood sample tube, said means for mounting said double-ended hollow needle including a connector mounted in said closed end wherein it may be rotatably adjusted with respect to the cylindrical body to enable rotatable adjustment of said needle.

2. A blood extraction instrument in accordance with claim 1 wherein said connector is provided with a ring-type structure, provided with a hub with a retaining bead on the end thereof.

3. A blood extraction instrument in accordance with claim 2 wherein said hub with the retaining bead is forced into an aperture in the closed end of the cylindrical body and retained therein by said retaining bead.

4. A blood extraction instrument in accordance with claim 3 wherein said aperture in said closed end of said cylindrical body is provided with the radial slots enabling the entry of said hub with the bead thereon.

5. A blood extraction instrument in accordance with claim 3 wherein said hub and bead are provided with radial slots therein enabling the compression of said hub to fit into said aperture of said cylindrical body.

6. A blood extraction instrument in accordance with claim 1 wherein the outer contour of the adjustably rotatable connector extends beyond the outer edge of the cylindrical body at at least one point thereby facilitating manual rotatable adjustment.

7. A blood extraction instrument in accordance with claim 1 wherein the edge of the connector is provided with a knurling to aid in rotatable adjustment of the connector.

8. A blood extraction instrument in accordance with claim 1 wherein a retaining tongue is provided in the cylindrical wall of the cylindrical body, said retaining tongue in its normal position does not obstruct insertion or removal of said blood sample tube, but which may be bent inwardly against a resilient force towards the interior of said cylindrical body sufficient to grip behind said screw-on cap of said blood sample tube when said blood sample tube is inserted in the cylindrical body and secure said blood sample tube in the cylindrical body to prevent it from falling out.

9. A blood extraction instrument in accordance with claim 8 wherein said retaining tongue is formed by a slot in the cylindrical wall of said cylindrical body.

10. A blood extraction instrument in accordance with claim 9 wherein the resilient force retaining said tongue in its normal position is reinforced by a rib formed on said tongue.

* * * * *